US005492718A

United States Patent [19]

O'Neill et al.

[11] Patent Number: 5,492,718
[45] Date of Patent: Feb. 20, 1996

[54] FLUID DELIVERY APPARATUS AND METHOD HAVING AN INFRARED FEEDLINE SENSOR

[75] Inventors: James A. O'Neill, New City; Michael L. Passow, Pleasant Valley; Tina J. Cotler, Newburgh; Jonathan D. Chapple-Sokol, Poughkeepsie; Richard A. Conti, Mount Kisco; Jyothi Singh, Hopewell Junction, all of N.Y.

[73] Assignee: International Business Machines Corporation, Armonk, N.Y.

[21] Appl. No.: 349,230

[22] Filed: Dec. 5, 1994

Related U.S. Application Data

[62] Division of Ser. No. 143,228, Oct. 29, 1993.

[51] Int. Cl.$^6$ .............................. B05D 3/06; C23C 8/00
[52] U.S. Cl. ................................ 427/8; 427/585
[58] Field of Search ............................ 427/8, 10, 585; 118/689, 690, 691; 73/64.43

[56] References Cited

U.S. PATENT DOCUMENTS

| | | | |
|---|---|---|---|
| 3,654,109 | 4/1972 | Hohl et al. | 204/192 |
| 3,695,764 | 10/1972 | Delmas et al. | 356/97 |
| 3,734,620 | 5/1973 | Cade | 356/73 |
| 3,808,436 | 4/1974 | Risgin et al. | 250/344 |
| 4,049,352 | 9/1977 | Lardon | 356/73 |
| 4,100,310 | 7/1978 | Ura et al. | 427/8 |
| 4,388,342 | 6/1983 | Suzuki et al. | 427/8 |
| 4,478,173 | 10/1984 | Doehler | 118/688 |
| 4,649,711 | 3/1987 | Sibley et al. | 62/129 |
| 4,849,259 | 7/1989 | Biro et al. | 427/248.1 |
| 4,888,199 | 12/1989 | Felts et al. | 427/10 |
| 5,032,435 | 7/1991 | Biefeld et al. | 427/8 |
| 5,073,232 | 12/1991 | Ohmi et al. | 156/646 |
| 5,101,764 | 4/1992 | Loewenstein et al. | 118/712 |

FOREIGN PATENT DOCUMENTS 0370311  5/1990  European Pat. Off. .
WO90/04164  4/1990  WIPO .

OTHER PUBLICATIONS

Patent Abstracts of Japan, vol. 9, No. 108 (C–280) 11 May 1985 & JP-A-60 002 667 (Kokusai Denki) 8 Jan. 1985 (Abstract).
Patent Abstracts of Japan, vol. 4, No. 1, (E–163) 8 Jan. 1980 & JP-A 141 194 (Fujitsu) 11 Feb. 1979 (Abstract).
Advances in Instrumentation and Control, vol. 44, No. 1, 1989, Research Triangle Park, U.S. pp. 325–329, T. M. Cardis "Continuous composition measurements with a new process photometer" (Abstract).
Journal of Crystal Growth 77 (1986) 163–171 North–Holland Amsterdam by J. E. Butler, et al., entitled "In Situ, Real–Time Diagnostics of OMVPE Using Ir–Diode Laser Spectroscopy".
Journal of Crystal Growth 77 (1986) 73–78 North–Holland Amsterdam by R. S. Sillmon, et al., entitled "An Ultra–Fast Gas Delivery System for Producing Abrupt Compositional Switching in OMVPE".

(List continued on next page.)

Primary Examiner—Shrive Beck
Assistant Examiner—Fred J. Parker
Attorney, Agent, or Firm—Aziz M. Ahsan; Harold Huberfeld

[57] ABSTRACT

An apparatus for processing a layer on a workpiece includes a source of reactant fluid, a reaction chamber having a support for the workpiece and a fluid delivery apparatus for feeding an input fluid into the reaction chamber with the input fluid being utilized to process the material. An infrared sensor is adapted to cooperate with the fluid delivery apparatus for sensing the concentration of a component of the input fluid. The infrared sensor includes an infrared light source positioned to direct a beam of infrared light at an infrared light detector through the input fluid. The infrared light detector produces an electrical output signal indicative of the amount of light received by the detector and therefore not absorbed by the input fluid.

16 Claims, 8 Drawing Sheets

OTHER PUBLICATIONS

J. Vac. Sci. Technol. A3(6), Nov./Dec. 1985, pp. 2205–2208 by E. M. van Veldhuizen, et al., entitled "Absolute Densities of Reaction Products from Plasma Etching of Quartz".

*Paper presented at the Fifth Symposium on Ion Sources and Ion–assisted Technology and International Workshop on Ion–based Techniques for Film Formation, Tokyo and Kyoto, Japan, Jun. 1–5, 1981. by J. Nishizawa, et al., entitled "In Situ Observation of Plasmas for Dry Etching by IR Spectroscopy and and Probe Methods*", pp. 189–198.

FLUID DELIVERY APPARATUS AND METHOD HAVING AN INFRARED FEEDLINE SENSOR

CROSS-REFERENCE TO APPLICATION

This application is a divisional of application Ser. No. 08/143,228 filed Oct. 28, 1993.

The present invention relates generally to a fluid delivery apparatus and method and more particularly to an apparatus and method for monitoring and controlling the concentration of a compound of a gas delivered to a chamber for manufacturing microelectronic devices.

BACKGROUND OF THE INVENTION

The development and parameter optimization of CVD and etch processes used in the manufacture of microelectronic devices has heretofore been accomplished to a large extent by empirical techniques, such as the use of monitor and send-ahead wafers. The use of such techniques has been necessitated because no reliable method has existed to measure and control certain key process parameters, such as the deposition rate and quality of a deposited film, as they are changing during the process, i.e., in real-time. This problem has been particularly true in those CVD processes which use precursor gases derived from liquid or solid sources to form the deposited film. For example, CVD processes which use tetraethoxysilane (TEOS) to deposit oxide films have attained widespread use as described in U.S. Pat. No. 4,849,259 to Biro et al. Condensible gases have also frequently been used as a source of phosphorous or boron in the formation of doped oxide films. Such condensible feedgases are frequently derived by bubbling a carrier gas through a reservoir of liquid precursor or passing a carrier across a solid precursor held at a temperature necessary to maintain an adequate vapor pressure. The gas entrained in this manner is then delivered to a reaction chamber through heated delivery lines (see the aforementioned U.S. Pat. No. 4,849,259). In an alternate method, undiluted vapor may be delivered to a reaction chamber without the use of a carrier gas. Applicants have discovered that the quality of the film deposited and the film deposition rate in such CVD processes are a function of the concentration of the feedgas. The feedgas concentration is in turn a sensitive function of the thermal stability of the liquid source and the delivery apparatus, the level of the liquid in the reservoir and the rate of flow of the carrier gas. Thus in the absence of a means to measure the concentration of such condensible feedgases in real-time, it has heretofor been necessary to employ costly and time consuming empirical techniques to control such CVD processes.

SUMMARY OF THE INVENTION

Accordingly, an apparatus and method are provided for processing a layer on a workpiece. The apparatus includes a source of reactant fluid, a reaction chamber having a support for the workpiece and fluid delivery means for feeding an input fluid into the reaction chamber with the input fluid being utilized to process the material. The fluid delivery means includes a first conduit in fluid communication with the source of reactant fluid and a second conduit in fluid communication with the reaction chamber. An infrared sensor is serially connected between and in fluid communication with the first and second conduits for sensing the concentration of a component of the input fluid. The infrared sensor includes an infrared light source and an infrared light detector, with the infrared light source being positioned to direct a beam of infrared light at the infrared light detector through the input fluid. The infrared light detector includes means for producing an electrical output signal indicative of the amount of infrared light received by the detector. The fluid delivery means includes a first conduit adapted to have the input fluid flow therethrough, with the first conduit being in fluid communication with the infrared sensor. A second conduit is in fluid communication with the infrared sensor for permitting the fluid sensed by the infrared sensor to flow therethrough. The method is a method of processing a layer of material on a workpiece and includes supporting the workpiece in a reaction chamber and feeding an input fluid into the reaction chamber to process the material. The method further includes sensing the concentration of the input fluid by directing a beam of infrared light through the input fluid, detecting the amount of the beam of infrared light not absorbed by the input fluid and producing an electrical output signal indicative of the non-absorbed light.

Accordingly a feature of the present invention is the provision of a CVD or etch apparatus and method which eliminates the need for empirical testing to optimize manufacturing parameters.

Another feature of the present invention is the provision of a fluid delivery apparatus which may be easily and inexpensively coupled to a CVD or etch apparatus to achieve the aforementioned feature.

Other advantages and novel features of the present invention will become apparent from the following detailed description of the invention when considered in conjunction with the accompanying drawings.

DESCRIPTION OF THE PREFERRED EMBODIMENTS

Figure 1:
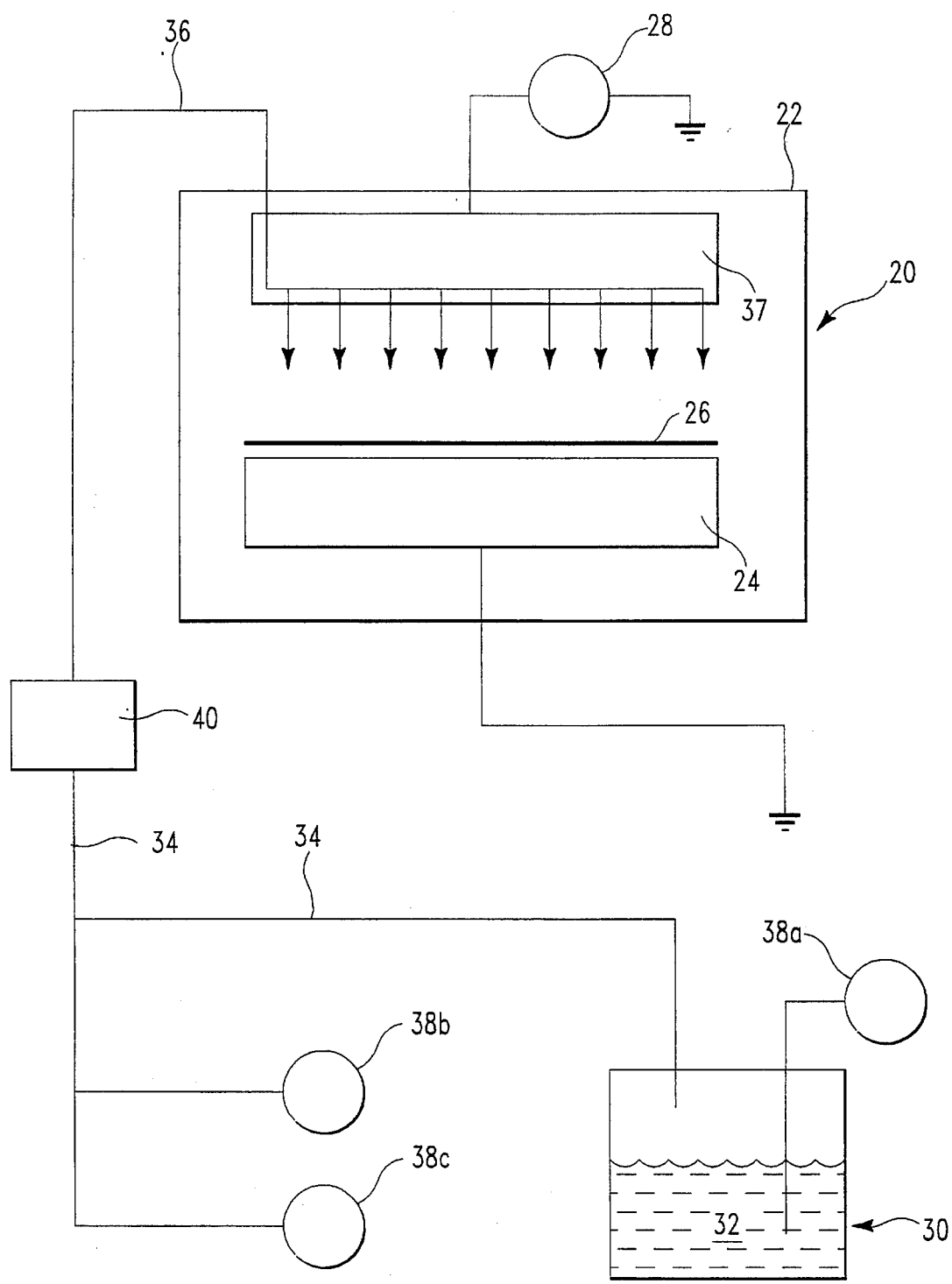
FIG. 1 shows a schematic diagram of a first embodiment of a CVD apparatus of the present invention.

FIG. 1 shows a CVD or etch reactor 20 having a reaction chamber 22, preferably a plasma reactor, including a holder 24, preferably an electrostatic chuck, for supporting a workpiece 26. The workpiece 26 is typically a semiconductor wafer constituting an intermediate work product in the manufacture of microelectronic devices. The plasma in reaction chamber 22 is generated by an RF source 28. The apparatus further includes a reservoir 30 containing a reactant liquid (or solid) 32. A conduit 34 has one end thereof placed over the reactant 32 and serves to carry gas generated by the reactant 32 to a second conduit 36, which in turn is in fluid communication with the reaction chamber 22 preferably through a manifold 37. A carrier gas such as He is delivered from a source 38a to the reactant 32, for example, liquid TEOS resulting in a mixture of TEOS and He in conduit 34. Additional components such as $O_2$ and $O_3$ may be added to conduit 34 from sources 38b and 38c respectively. An infrared sensor 40 is interposed between and in fluid communication with the conduits 34 and 36 for sensing the concentration of the input gas flowing in conduits 34 and 36 to reaction chamber 22. The infrared sensor 40 may be any one of the following embodiments of the present invention.

Figure 2:
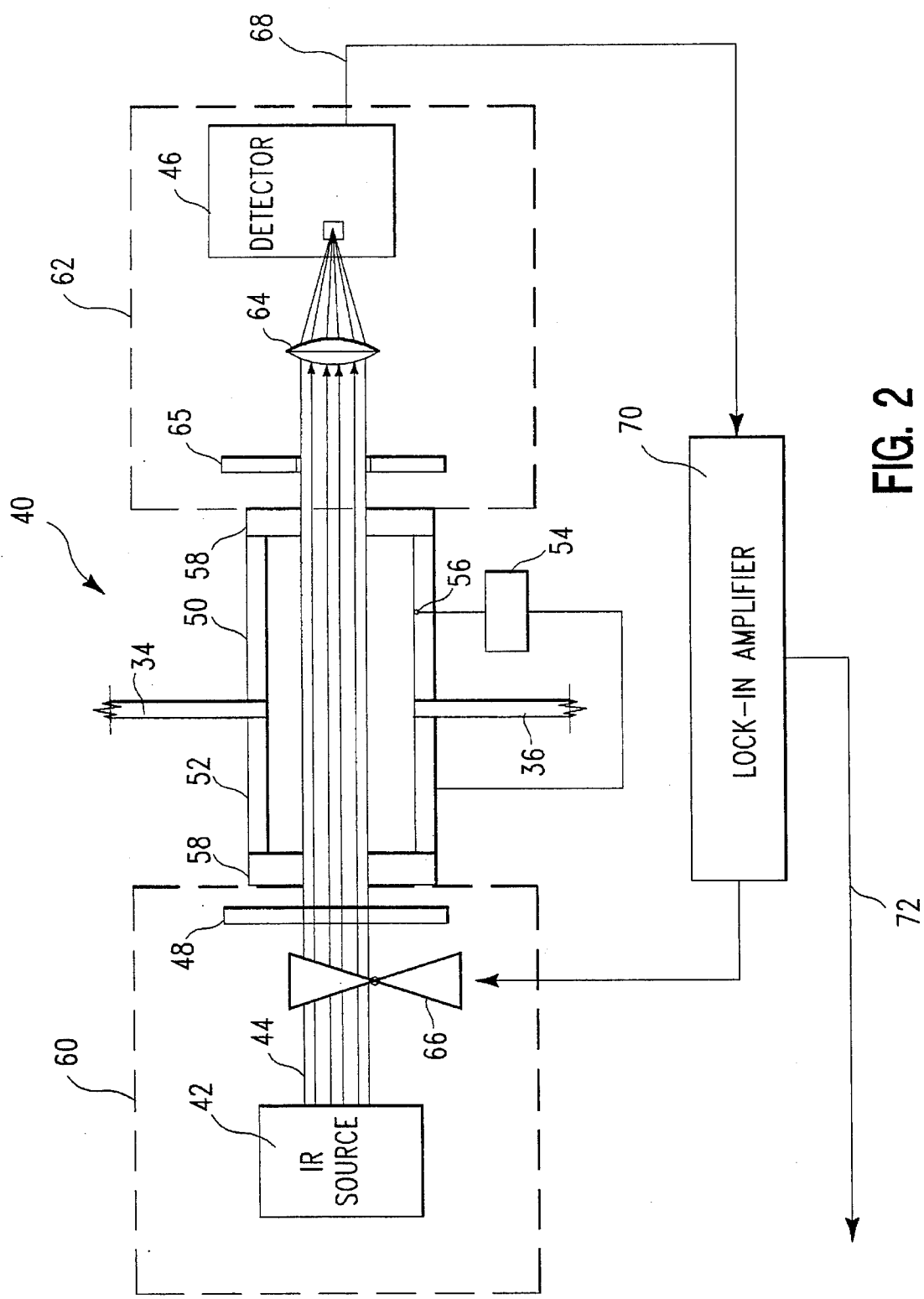
FIG. 2 shows a schematic diagram of an infrared sensor useful with the apparatus of FIG. 1.

FIG. 2 shows a general schematic diagram of an infrared sensor 40 of the present invention. The sensor 40 includes an infrared light source 42 positioned to direct a beam 44 of infrared light at an infrared light detector 46. The infrared light source 42 is preferably a hot filament which emits radiation having a wavelength in a desired range of infrared wavelengths. The wavelength of the beam 44 is determined by an infrared interference filter 48 positioned in the path of the beam 44 and selected for the detection of a single gas species of interest. The bandwidth of the filter 48 is equal to or less than 100 $cm^{-1}$ centered about the wavelength of the selected species. The beam 44 passes through a stainless steel gas sample cell 50 maintained at a desired temperature by a thermally insulated heating mantle 52 connected to and controlled by a temperature controller 54. The temperature controller 54 utilizes a thermocouple 56 on the surface of cell 50 to monitor the cell temperature. The beam 44 is passed through a pair of infrared transparent windows 58 mounted on the ends of the cell 50 by suitable flanges and retaining screws. The windows 58 are made of a material selected to optimize transparency at the selected wavelength of beam 44. For example, this material may be ZnSe, ZnS, Ge, KCl, KRS-5, AgCl, AgBr, $Al_2O_3$, $MgF_2$ or $CaF_2$. The infrared light source 42 is mounted in a housing 60 adapted to engage one of the flanges on cell 50 to retain one window 58 in a wall of housing 60. Likewise the detector 46 is mounted in a housing 62 adapted to engage the other flange on cell 50 to retain the other window 58 in a wall of housing 62. The cell 50 is coupled to and in fluid communication with the conduit 34 delivering input gas from reservoir 30 and the conduit 36 delivering the input gas to reaction chamber 22. Condensation of input gas on the windows 58 is eliminated by providing appropriate insulation on the flanges of cell 50 and by setting temperature controller 54 to maintain cell 50 at a slightly higher temperature than the conduits 34 and 36 and the other components in the gas delivery apparatus 40. The dimensions of the cell 50 are a function of the particular input gas and its partial pressure. The beam 44 is focussed on the detector by a lens 64 after passing through an iris 65, both mounted in housing 62. The intensity of beam 44 is modulated with an optical chopper 66 mounted in housing 60. Detector 46 produces an electrical output signal on line 68 indicative of the amount of infrared light received by the detector. The detector 46 is preferably a pyroelectric infrared detector. The concentration of a particular input gas is measured by the amount of light reaching the detector 46 and therefore not absorbed by the input gas. As will be described in greater detail in subsequent embodiments, the electrical output signal on line 68 is delivered to and demodulated by a lock-in amplifier 70 tuned to the frequency of the optical chopper 66. The output 72 of amplifier 70 is then processed as will be hereinafter described.

Figure 3:
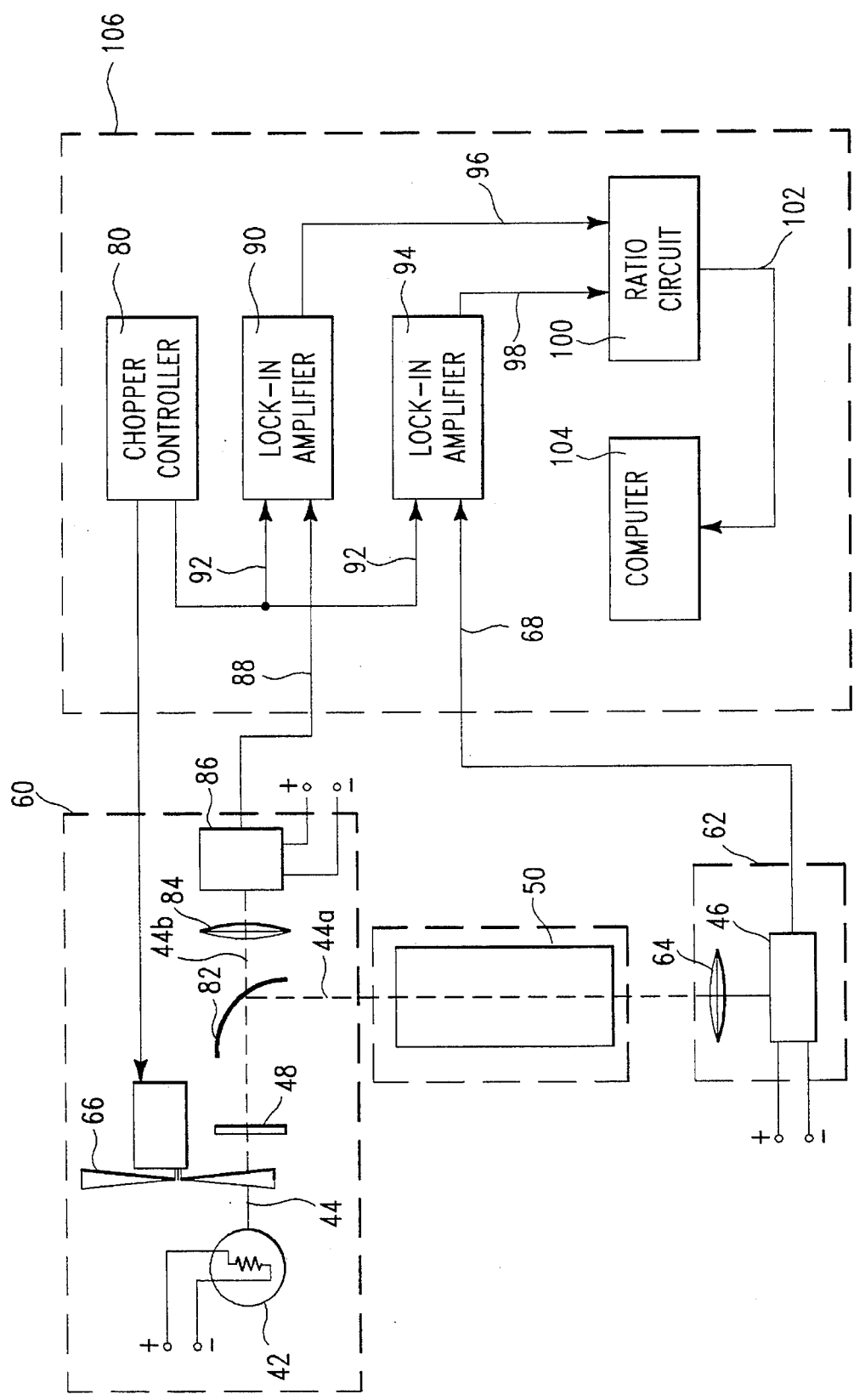
FIG. 3 shows a schematic diagram of the infrared sensor shown in FIG. 2 in greater detail.

In the embodiments shown in FIG. 3, the infrared light source 42 emits a beam 44 which passes through the chopper 66, which is controlled by a chopper controller 80. The beam of infrared light 44 is modulated by chopper 66, filtered by filter 48, as discussed earlier, and directed toward an off-axis parabolic reflector 82 which serves to collimate any divergence in the beam 44 and redirect most of the beam 44 as beam 44a out of the housing 60 to the heated gas sample cell 50. A small portion 44b of the beam 44 passes through a hole in the reflector 82 and is directed through a focusing lens 84 to a detector 86. The optical signal 44b serves as an optical reference signal which is converted by detector 86 to an electrical reference signal 88 which is connected to a lock-in amplifier 90. The lock-in amplifier 90 also receives a reference signal 92 from chopper controller 80 indicative of the modulation frequency of chopper 66. The detector 86 is also preferably a pyroelectric infrared detector. As was described earlier in connection with FIG. 2, the beam 44a passes through a lens 64 to detector 46. The electrical output signal 68 from detector 46 is delivered to another lock-in amplifier 94. The lock-in amplifier 94 also receives signal 92 from chopper controller 80. The lock-in amplifier 90 demodulates and amplifies the reference signal 88 and produces an output reference signal 96. The lock-in amplifier 94 demodulates and amplifies the electrical output signal 68 and produces a demodulated electrical output signal 98. A ratio circuit 100 is connected to and takes the ratio of the signals 96 and 98 and produces a ratio output signal 102 which is then delivered to a recording apparatus such as a personal computer 104. The chopper controller 80, lock-in amplifiers 90 and 94, ratio circuit 100 and personal computer 104 are preferably housed in a single housing 106. The lock-in amplifiers 90 and 94 and the ratio circuit 100 are known designs.

Figure 4A:
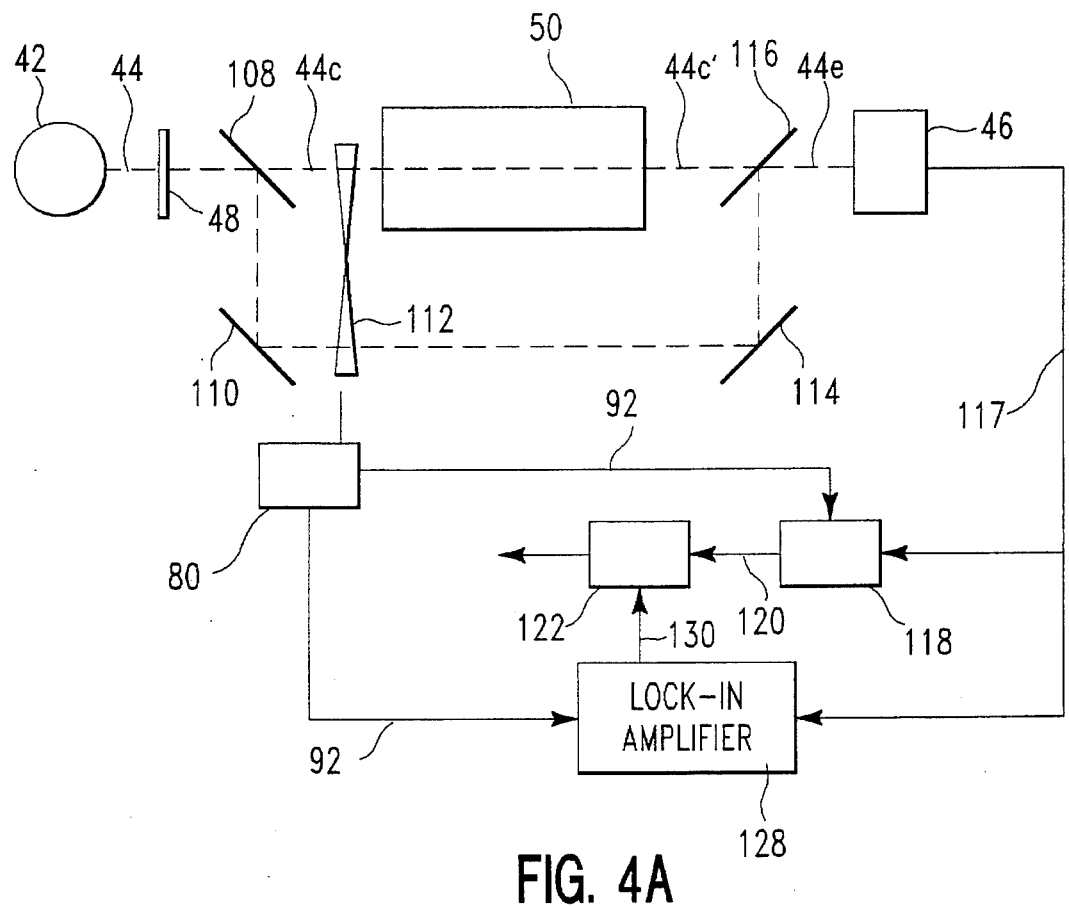
FIGS. 4A–4D show a schematic diagram and graphs of a second embodiment of an infrared sensor of the present invention.
Figure 4B:
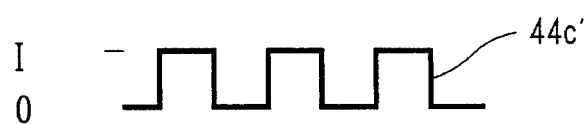
Figure 4C:
Figure 4D:

In the embodiment shown in FIG. 4A, the apparatus of the present invention is somewhat simplified. In this embodiment the infrared beam 44 is passed through a filter 48 and then through a beam splitter 108. The beam splitter 108 serves to separate the beam 44 into two beams, 44c and 44d. The beam 44c and the beam 44d, through suitable reflecting means such as a mirror 110, are then passed through a modified chopper 112. The chopper 112 is designed to alternately modulate the signals 44c and 44d, i.e., only one of the beams 44c and 44d passes through the chopper at any point in time. In its simplest form, the chopper 112 is a disk which is opaque on fifty percent of its surface and transmissive on the remaining fifty percent with respect to infrared radiation. As shown in FIG. 4A, the modulated signal 44c is passed through the heated sample cell 50 to thereby deliver the modulated signal 44c' to detector 46 through a beam splitter 116. As shown in FIG. 4B, the modulated signal 44c' varies between zero and I in intensity. Likewise, the signal 44d is reflected to detector 46 by elements 114 and 116 so as to be added to signal 44c'. The signal 44d is shown in FIG. 4C and varies between zero and the reference intensity $I_0$ and is 180° out of phase with the signal 44c'. The resultant signal 44e is shown in FIG. 4D and varies in intensity between I and $I_0$. The detector 46 then produces an electrical output signal 117 representative of optical input signal 44e. The signal 117 is first delivered to a circuit 118 which is synchronized with chopper 80 by signal 92 to deliver an output signal indicative of $I_0$, the reference intensity. The output 120 of circuit 118 is delivered to a ratio circuit 122. In like manner, the output, signal 117 of detector 46 is delivered to a lock-in amplifier 128 which is synchronized with chopper 80 to produce an output 130 indicative of the demodulated value of $I_0-I$. The ratio circuit 122 then takes the ratio of the outputs 120 and 130, $(I_0-I):I_0$, and delivers them to a recording device as before.

Figure 5A:
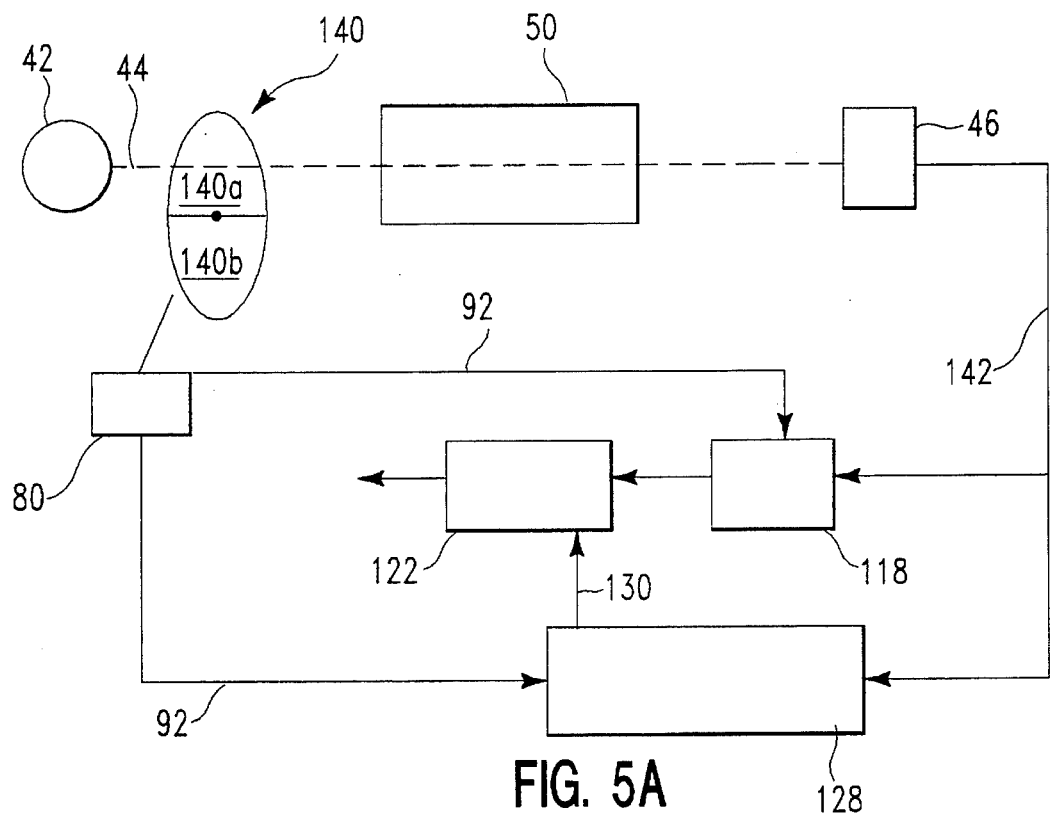
FIGS. 5A–5C show a schematic diagram and graphs of a third embodiment of an infrared sensor of the present invention.
Figure 5B:
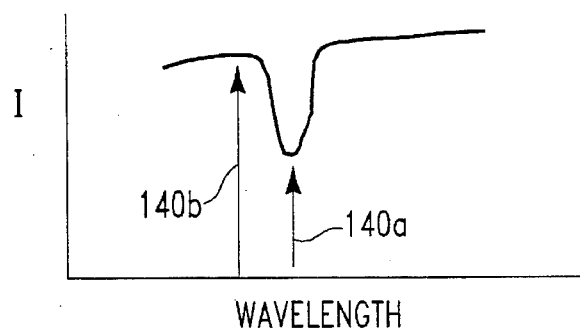
Figure 5C:
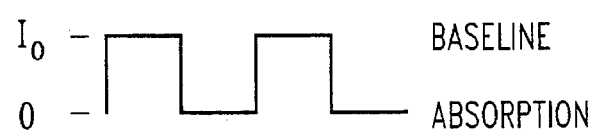

In the embodiment shown in FIG. 5A, the embodiment shown in FIG. 4A is further modified and simplified by utilizing a rotating element 140 as an optical chopper. The rotating element 140 is positioned in the path of the beam 44 such that a filter 140a is rotated into the path of the beam 44 during half the cycle and a filter 140b is rotated into the path of the beam 44 by the other half of the cycle. The filter 140a has a bandwidth equal to or less than 100 cm$^{-1}$ centered about a predetermined wavelength in the infrared range which will be absorbed by the gas species in cell 50. The filter 140b, on the other hand, is centered about a second wavelength which is designed not to be absorbed by the input gas in cell 50. Thus, light passing through filter 140b serves as an optical reference signal when delivered to the detector 46. FIG. 5B shows a spectrum illustrating the difference in the outputs from filter 140b and filter 140a. Thus, the output 142 from detector 46 as shown in FIG. 5C is also a square wave having a maximum amplitude of $I_0$ and a minimum amplitude of I. In all other respects the circuit of FIG. 5A operates in like manner to that of FIG. 4A.

Figure 6:
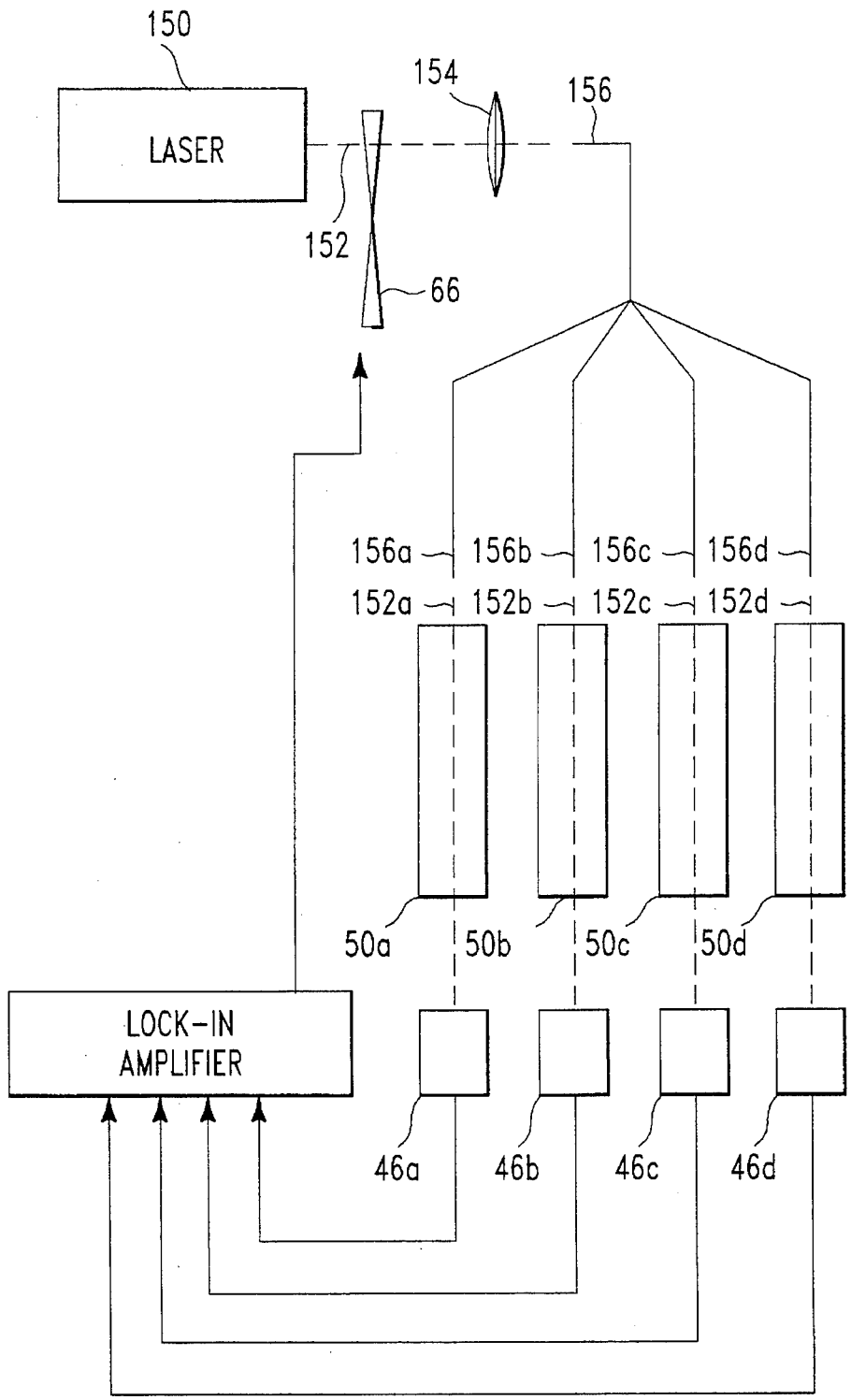
FIG. 6 shows a schematic diagram of a fourth embodiment of an infrared sensor of the present invention.

FIG. 6 shows an embodiment of the apparatus of the present invention wherein the infrared light source is a laser 150 tuned to a predetermined wavelength in the infrared range. This embodiment has the advantage that the bandwidth of laser 150 can be much narrower than the bandwidth of the various infrared filters utilized in the embodiments heretofore described. The output 152 of laser 150 is modulated by chopper 66 and focussed by a lens 154 on an optical fiber 156. This approach has the additional advantage that the output 152 has sufficient power if so desired to be divided into a plurality of signals 152a, 152b, 152c, and 152d and thus be delivered along a plurality of fibers 156a, 156b, 156c and 156d to a plurality of sample cells 50a through 50d as shown in FIG. 6. In like manner, such a system would include a plurality of detectors 46a through 46d. Thus a single laser 150 could serve as the infrared light source for a plurality of deposition and/or etch apparatus.

Figure 7:
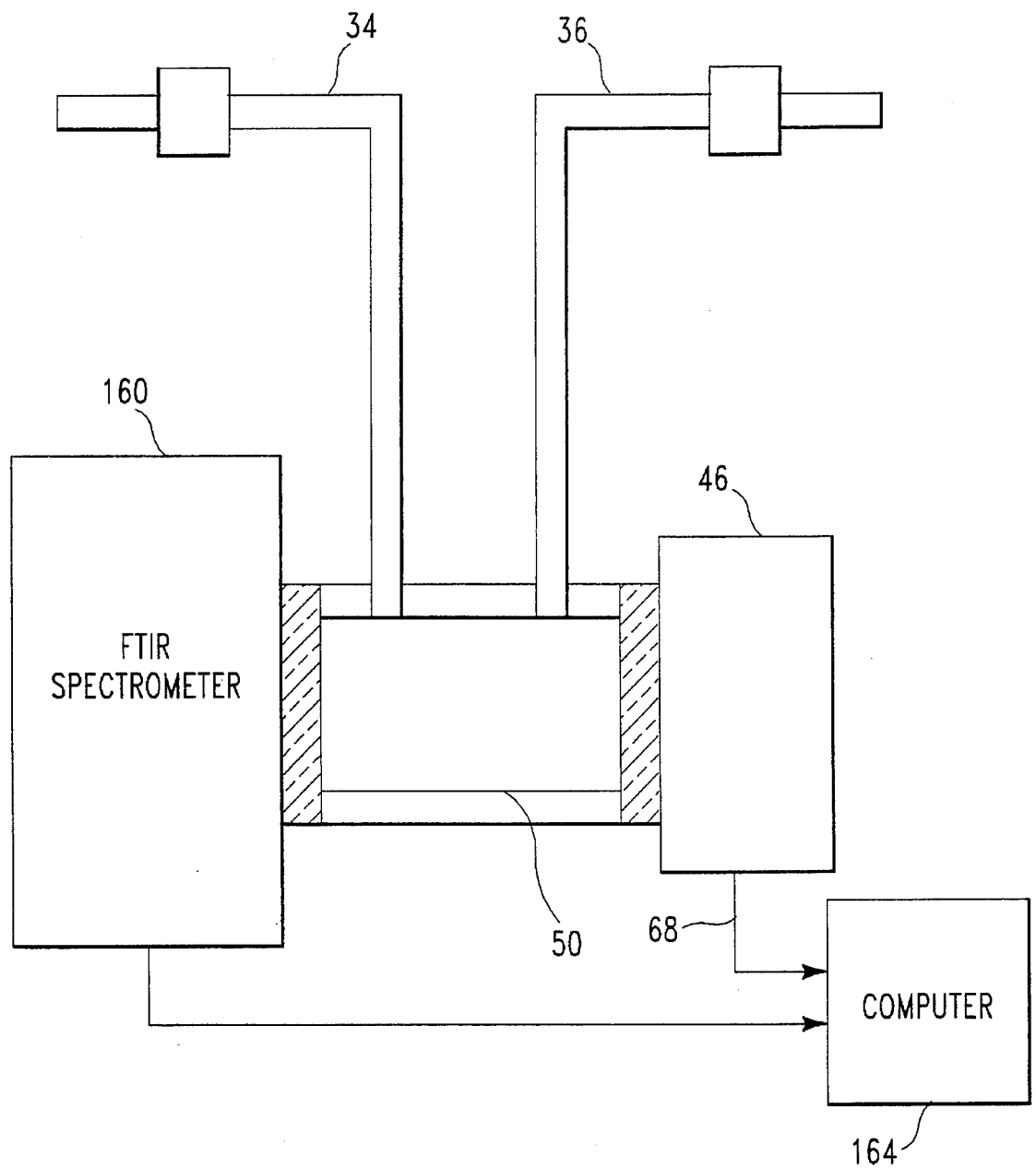
FIG. 7 shows a schematic diagram of a fifth embodiment of an infrared sensor of the present invention.

FIG. 7 shows another embodiment of the present invention wherein the infrared light source is a Fourier transform infrared spectrometer 160. The output of the spectrometer 160 is passed through the cell 50 to the infrared detector 46. The infrared spectrometer 160 also includes an electrical output 162 which along with the output 68 from detector 46 is fed to a computer 164 for deriving the concentration of the input gas therefrom.

Figure 8:
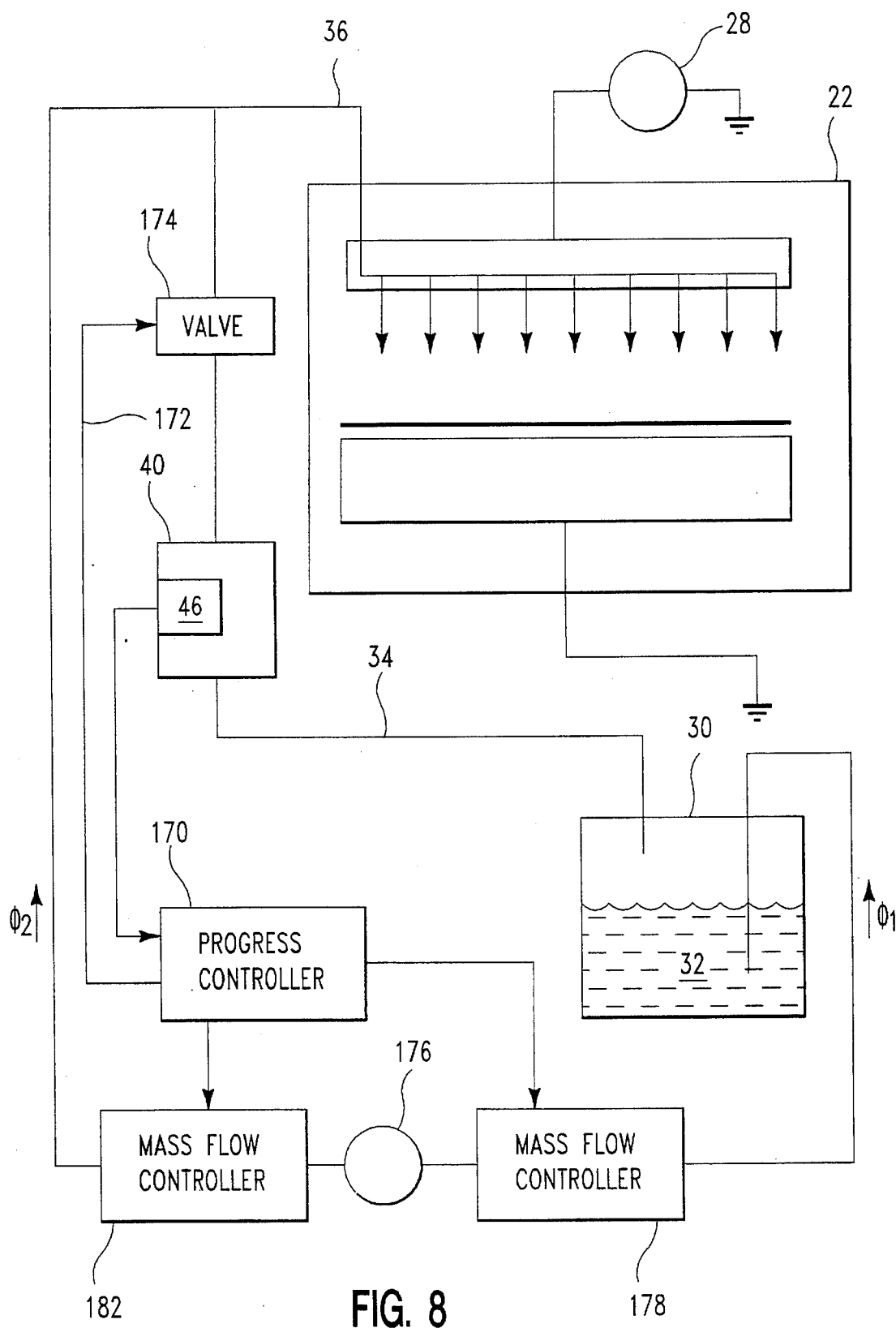
FIG. 8 shows a block diagram of a control system useful with the gas delivery apparatus of the present invention.

The computer 104 and the associated controller, amplifiers, and circuitry housed in housing 106 in the embodiment shown in FIG. 3 and the alternative embodiments shown in FIGS. 4–7 and the computer 164 in the embodiment shown in FIG. 7 essentially serve as a process controller. In FIG. 8, this process controller 170 in its simplest mode calculates the flow of input gas from the concentration measured by detector 46, integrates the result versus time and adjusts the time of the deposition or other process parameters (e.g. deposition or etch rate) accordingly by comparing the measured data from the detector 46 with a library of reference data which may be empirically and/or theoretically obtained. When the process is to be terminated, the controller 170 sends a signal on line 172 to close a valve 174 in conduit 36 leading to reaction chamber 22 or performs another similar function which effectively terminates the process in reaction chamber 22. Thus in FIG. 8, an apparatus is shown in block diagram form wherein the gas delivery means includes a control apparatus responsive to the electrical output signal from the detector 46 for controlling the rate of flow of the input gas into the reaction chamber 22. A carrier gas at a flow rate $\phi_1$ is supplied by a source 176 and delivered by a mass flow controller 178 to reactant liquid 32 in reservoir 30. Simultaneously, a diluent gas at a flow rate $\phi_2$ is supplied by the source 176 and delivered by a mass flow controller 182 to conduit 36. The flow of input gas in conduit 34 is calculated as before. The process controller 170 then adjusts the flow $\phi_1$ of the carrier gas by means of controller 178 to maintain the flow of input gas constant. Simultaneously, the process controller 170 adjusts the flow $\phi_2$ of the diluent gas by means of controller 182 to maintain $\phi_1+\phi_2$ constant. The process is then terminated as before by closing valve 174 when a desired film thickness is reached as calculated by the desired flow of input gas at a desired concentration of reactant gas for a measured period of time.

Thus a CVD or etch apparatus and method have been provided which minimize the need for empirical testing to optimize manufacturing parameters. The CVD or etch apparatus includes a gas delivery apparatus which may be easily and inexpensively coupled to the apparatus.

While there have been described what are at present considered to be the preferred embodiments of the present invention, it will be obvious to those skilled in the art that various changes and modifications may be made therein, without departing from the invention, and it is, therefore, aimed in the appended claims to cover all such changes and modifications as follow in the true spirit and scope of the present invention.

What is claimed is:

1. A method of processing a layer of material on a workpiece comprising:

supporting said workpiece in a reaction chamber;

feeding an input fluid from a source of reactant fluid into said reaction chamber to form said material;

situating an infrared sensor between said reaction chamber and said source of reactant fluid for sensing the concentration of a component of said input fluid by directing a beam of infrared light through a direct feed of all of said input fluid being fed from said source of reactant fluid to said reaction chamber, detecting the amount of the beam of infrared light not absorbed by said input fluid, and producing an electrical output signal indicative of said non-absorbed infrared light for sensing the concentration of a component of the input fluid delivered to said reaction chamber.

2. The method of claim 1, wherein said beam of infrared light directed through said input fluid is emitted in a range of infrared wavelengths.

3. The method of claim 2 further including filtering said beam of infrared light to a bandwidth not greater than 100 cm$^{-1}$ centered about a first characteristic wavelength in the infrared range.

4. The method of claim 2, further including focusing said beam of infrared light not absorbed by said input fluid on an infrared light detector.

5. The method of claim 2, further including modulating said beam of infrared light prior to its contacting said input fluid and demodulating said electrical output signal.

6. The method of claim 5, further including periodically filtering said beam of infrared light to a bandwidth not greater than 100 cm$^{-1}$ centered about a second wavelength in the infrared range to produce a reference signal.

7. The method of claim 6, further including converting said beam of infrared light, after said step of filtering, to an electrical signal, taking the ratio of said electrical signal and said demodulated electrical output signal and generating an output signal indicative of said ratio.

8. The method of claim 1, further including controlling the rate of flow of said input fluid into said reaction chamber.

9. The method of claim 8, wherein said input fluid is an input gas and wherein said step of controlling the rate of flow of said input gas includes comparing said electrical output signal to a library of infrared reference data.

10. The method of claim 9, wherein said step of controlling the rate of flow of said input gas includes controlling the rate of processing said layer of material.

11. The method of claim 9, wherein said source of reactant fluid is a reactant liquid and further including delivering a carrier gas to said reactant liquid at a first flow rate thereby generating a reactant gas, delivering a diluent gas to said reactant gas at a second flow rate and maintaining the sum of said first and second flow rates constant.

12. The method of claim 1, further including filtering said beam of infrared light to a bandwidth not greater than 100 $cm^{-1}$ centered about a first characteristic wavelength in the infrared range.

13. The method of claim 1, further including focusing said beam of infrared light not absorbed by said input fluid on an infrared light detector.

14. The method of claim 1, further including modulating said beam of infrared light prior to its contacting said input fluid and demodulating said electrical output signal.

15. The method of claim 1, further including periodically filtering said beam of infrared light to a bandwidth not greater than 100 $cm^{-1}$ centered about a second wavelength in the infrared range to produce a reference signal.

16. The method of claim 15, further including converting said beam of infrared light, after said step of filtering, to an electrical signal, taking the ratio of said electrical signal and said demodulated electrical output signal and generating an output signal indicative of said ratio.

* * * * *